(12) United States Patent
Feuerstein et al.

(10) Patent No.: US 8,240,312 B2
(45) Date of Patent: Aug. 14, 2012

(54) METHOD AND MEANS FOR EXERTING A PHOTOTOXIC EFFECT OF VISIBLE LIGHT ON MICROORGANISMS

(75) Inventors: Osnat Feuerstein, Jerusalem (IL); Ervin I. Weiss, Herzeliya (IL); Michael Perez Davidi, Savion (IL)

(73) Assignee: Osnat Feuerstein, Jerusalem (IL)

( * ) Notice: Subject to any disclaimer, the term of this patent is extended or adjusted under 35 U.S.C. 154(b) by 1860 days.

(21) Appl. No.: 10/936,816

(22) Filed: Sep. 9, 2004

(65) Prior Publication Data
US 2006/0085052 A1    Apr. 20, 2006

(51) Int. Cl.
*A61B 19/00*    (2006.01)
*A61N 5/06*    (2006.01)
(52) U.S. Cl. .......................................... 128/898; 607/88
(58) Field of Classification Search ................ 606/3–18; 607/88–94; 128/898
See application file for complete search history.

(56) References Cited

U.S. PATENT DOCUMENTS

| | | | |
|---|---|---|---|
| 4,784,135 A | 11/1988 | Blum et al. | |
| 5,611,793 A | 3/1997 | Wilson et al. | |
| 5,658,148 A | 8/1997 | Neuberger et al. | |
| 6,090,788 A * | 7/2000 | Lurie | 514/23 |
| 6,290,496 B1 * | 9/2001 | Azar et al. | 433/29 |
| 6,623,513 B2 * | 9/2003 | Biel | 607/88 |
| 6,676,655 B2 * | 1/2004 | McDaniel | 606/9 |
| 7,354,448 B2 * | 4/2008 | Altshuler et al. | 607/88 |
| 2003/0149129 A1 | 8/2003 | Dickens | |
| 2010/0076526 A1 * | 3/2010 | Krespi et al. | 607/88 |

FOREIGN PATENT DOCUMENTS

| | | |
|---|---|---|
| DE | 19950933 | 4/2001 |
| DE | 20209441 U | 9/2002 |
| EP | 1029880 | 8/2000 |
| WO | WO 01/55444 A1 | 8/2001 |
| WO | WO 02/096896 A1 | 12/2002 |

* cited by examiner

*Primary Examiner* — Ahmed Farah
(74) *Attorney, Agent, or Firm* — Wiggin and Dana LLP; Gregory S. Rosenblatt

(57) ABSTRACT

The present invention discloses a selective and a non-selective method and means of treating microbial diseases in local infections. The novel method comprising the step of emitting a beam of a blue light towards the tissue to be treated, wherein the beam is having a wavelength from 400 to 550 nanometers and further wherein the temperature of said tissue is not exceeding about 42° C. along the procedure or immediately after it so that a selective phototoxic effect is exerted. A cost effective device for selectively or non-selectively exerting phototoxic effect by emitting a beam of blue light towards a tissue to be treated is also provided useful, especially for dental application.

23 Claims, 5 Drawing Sheets

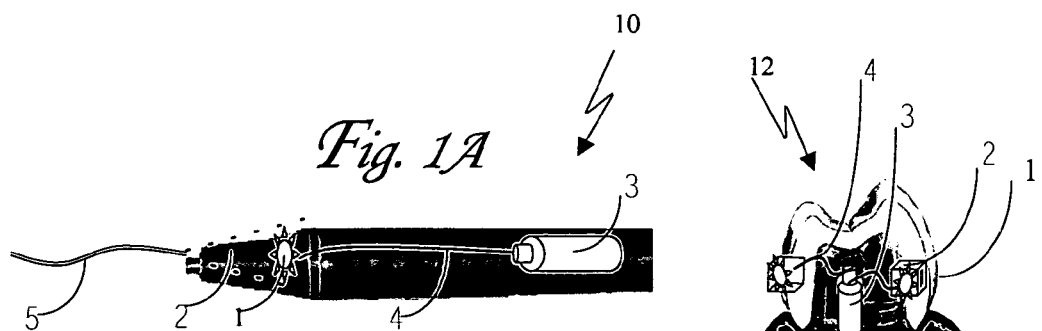
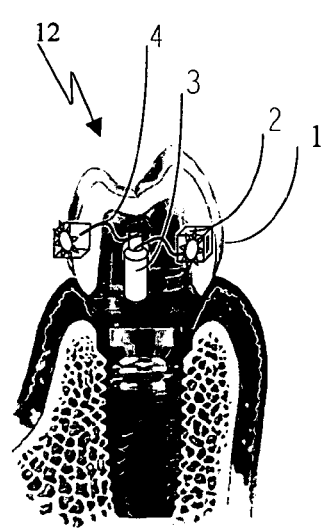
Fig. 1A
Fig. 1B
Fig. 1C
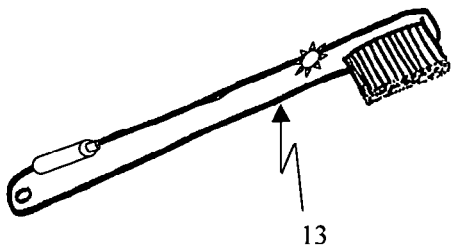
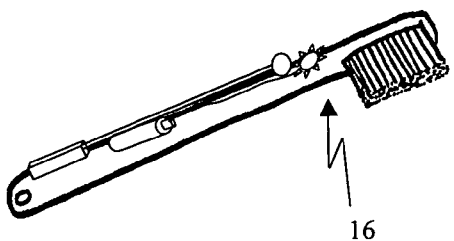
Fig. 1D
Fig. 1E
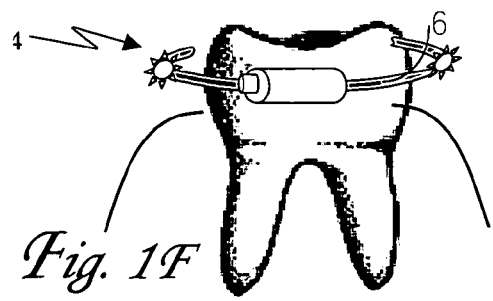
Fig. 1F
Fig. 1G

METHOD AND MEANS FOR EXERTING A PHOTOTOXIC EFFECT OF VISIBLE LIGHT ON MICROORGANISMS

FIELD OF THE INVENTION

The present invention generally relates to either a selective or non-selective method and means for exerting a phototoxic effect of visible light on microorganisms.

BACKGROUND OF THE INVENTION

Periodontal diseases are characterized by an inflammatory process in periodontal tissues caused by bacterial infection, resulting in the destruction of the periodontal soft tissue and alveolar bone. *Fusobacterium nucleatum*, for example, is an anaerobic Gram-negative non-sporeforming oral bacterium found in the normal flora of human mouth, that plays a major role in initiation and progression of periodontal diseases. The bacterium can adhere to a wide range of other major dental pathogen organisms, such as *Porphyromonas gingivalis*, and contribute to the development of periodontitis as well as invasive human infections of the head and neck, chest, lung, liver and abdomen.

Traditional approaches for reducing the bacterial load include mechanical removal and chemotherapy, the effectiveness of which is compromised by patient motivation, manual dexterity and the development of resistant species. In addition, the limited penetration of chemotherapeutic agents into bacterial biofilm results in reduced susceptibility to this kind of treatment.

Alternative approaches for reducing the bacterial load such as lethal photosensitization, using a photosensitizer in conjunction with visible light, have been suggested. Photosensitizers absorb an incident light that matches the wavelength of their peak absorption, results in killing of bacteria by a photochemical mechanism. The addition of exogenous photosensitizer to the target bacterial cells is required for lethal photosensitization. Nevertheless, some bacteria such as black-pigmented bacteroides possess endogenous porphyrins. Previous studies showed that low fluences of argon laser irradiation (wavelength, 488-514 nm) exert a phototoxic effect on *Porphyromonas* and *Prevotella* sp. *Propionibacterium acnes*, a Gram-positive porphyrine producing microorganism, was also inactivated by visible light without exogenous photosensitizer. Visible light (408-750 nm) was found mutagenic and caused metabolic and membrane damage of bacterial cells such as *Escherichia coli*, and a loss of colony-forming ability after illumination in seawater. The involvement of oxygen and reactive oxygen species (ROS) in the phototoxic effect of visible light on *E. coli* in seawater microcosms was shown. It has been demonstrated that ROS are also mediators of lethal photosensitization of *Streptococcus mutans*, in the presence of the light-activated toluidine blue O.

U.S. Pat. No. 5,611,793 to Wilson et al. discloses a method of disinfecting or sterilizing microbes infected tissues of the oral cavity by topically applying a photosensitising compound to the treated tissue and irradiating it with laser light, such as the red light helium neon gas lasers (632.8 nm) and gallium arsenide lasers (about 660 nm), at a wavelength absorbed by the photosensitising compound. A photosensitiser solution is administrated to contact with the microbes for a period of time to enable the microbes to take up some of the photosensitiser and become sensitive to the laser light. Then the laser light is introduced and the microbes are disinfected. Moreover, Wilson et al are stating in their patent that irradiation of both Gram-positive and Gram-negative oral bacteria in the absence of the photosensitisers had no detectable effect on the viability of these organisms.

U.S. Pat. No. 5,658,148 to Neuberger et al. discloses a method and a device for cleaning teeth by a low power diode laser applying the principle of photodynamic therapy. This method is based on using a photosensitizer compound. The photosensitizer compound produces singlet oxygen upon irradiation by the laser light. The singlet oxygen thus produced destroys oral bacteria.

Light is traditionally emitted in the oral cavity by various means, such as laser articulated arm, hollow fibers, fiber optics, and other tip instruments. Hence, U.S. Pat. No. 4,784,135 to Azar et al. teaches a toothbrush-like device wherein bacteria are stained preferably by applying a liquid or paste like formulation containing a bacterial selective dye within the oral cavity preferably followed by rinsing the oral cavity to wash out excess dye. The bacteria within the dental plaque are thus selectively stained by the dye and destroyed by visible light radiation.

Blue light (wavelength, about 400-500 nm) photocuring sources, such as the quartz-tungsten-halogen lamp (halogen lamp), the light emitting diode (LED) and the plasma-arc curing (PAC), are often used in dentistry for curing resin-composite materials. Non-coherent visible light kills *Porphyromonas* sp. presumably by a photochemical mechanism similar to that of argon laser. The toxic effect of visible light appears to be due to oxygen-dependent stimulation of ROS production.

A phototoxic effect of visible light sources mainly on the oxygen susceptible anaerobic bacteria, such as *P. gingivalis* and *F. nucleatum*, provided without utilizing any exogenous photosensitizers is hereto a long felt need.

SUMMARY OF THE INVENTION

It is thus the object of the present invention to provide a novel method for treating microbial diseases in local infections comprising the step of emitting a blue light beam towards the tissue to be treated without warming the tissue so that a selective or non-selective phototoxic effect is exerted. More specifically, the present invention provide either a selective or non-selective method for inhibit predetermined bacterial lawn from growing into biofilm such that periodontitis is prevented. This phenomenon could be enhanced in the presence of chemical cofactors such as oxygen precursors for ROS production.

Another object of the present invention is to provide a cost effective and easily used device for selectively or non-selectively exerting selective phototoxic effect by emitting a beam of a blue light towards a tissue to be treated. This device is preferably comprised of effective means for emitting at least one beam which having a wavelength from 400 to 550 nanometers such that the temperature of said tissue is not exceeding threshold causing an irreversible damage to the tissue; usually 42° C., along the procedure or immediately after it. This device is optionally combined with other means that increase the level of applied chemical cofactor in the target tissue.

The application of selective treatment method and means thereof and non-selectivity method and means thereof is provided inter alia by regulating the levels of parameters selected from blue light fluency; time of light exposure; oxygen donor and/or chemical cofactor efficiency and/or concentration or any combination thereof.

BRIEF DESCRIPTION OF THE DRAWINGS

In order to understand the invention and to see how it may be implemented in practice, a plurality of embodiments will now be described, by way of non-limiting example only, with reference to the accompanying drawing, in which FIGS. 1A-D schematically present blue light-emitting devices (10-15) according to several embodiments the present invention; FIG. 1A is lateral cross section of a device having flexible means to emit blue light beam from an emitting tip at the distal portion of the device, FIG. 1B is a cross section of a dental scaler having the same means for emitting blue light beam; FIG. 1C is a cross section view of a dental implant having the same means for emitting a blue light beam; FIG. 1D is a side view of a toothbrush comprising a blue light emitter; FIG. 1E is a side view of a similar toothbrush comprising a blue light emitter a means for applying an oxygen donor; FIG. 1F is a side view of a tooth cup comprising a ring-type blue light emitter; and FIG. 1G is a side view of a tray for tooth whitening comprising a blue light emitter;

DETAILED DESCRIPTION OF THE INVENTION

Figures 2A, 2B, 2C, 2D, 2E:
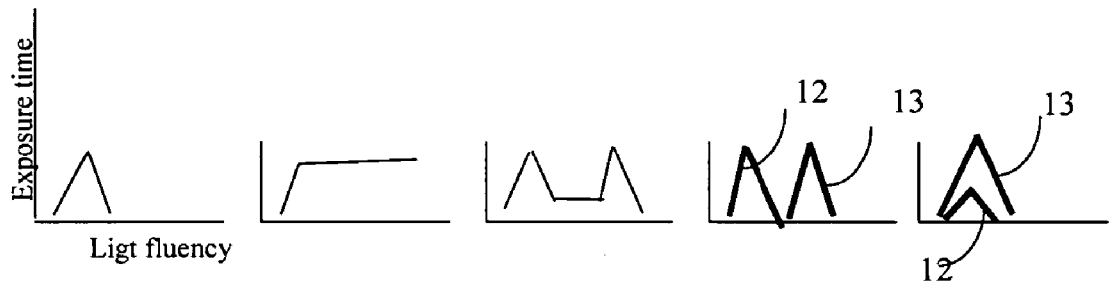
FIGS. 2A-E schematically present a light fluency vs exposure time diagrams according to several embodiments of the present invention, wherein for all diagrams X axis is the exposure time and Y axis is the light fluency.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a method and means for exerting a selective photochemical effect, and to discloses an effective means for inhibiting predetermined bacterial lawn (such as *Fusobacterium nucleatum* and *Porphyromonas gingivalis*) from growing into biofilm such that periodontitis is prevented.

Hence, the present invention provided a selective photochemical effect on microorganisms in local infections by selectively damaging specific bacteria comprising the steps of emitting a beam of a violet-blue light towards the tissue to be treated. This violet-blue beam is having a wavelength from about 400 to about 550 nanometers and refers hereinafter to the terms 'blue light or 'blue beam' etc. Said beam of blue light delivers variable energy densities to the tissue such that the temperature of said tissue not to exceed about 42° C. degrees such that an irreversible damage to the tissue during and after the step of emitting blue light is prevented. The step of emitting the blue light beam is utilized without any exogenous photosensitizers such that (i) a selective photochemical effect is exerted; and, (ii) no thermal coagulation of the bacteria is obtained. As used herein, the term "photochemical" refers to a chemical reaction which involves the interactions between molecules and light. More specifically, the photochemical reaction relates to a reaction that proceeds with the absorption of light. The term "selective method" refers hereinafter to a method for damaging specific bacteria more than other bacteria.

It is in the scope of the present invention wherein the aforesaid local infections are selected in a non-limiting manner from the body cavities or orifices; and further wherein the microbial diseases are selected inter alia from bacterial, viral or fungal diseases.

It is one of the objects of the present invention to provide a method for inhibit predetermined bacterial lawn from growing into oral biofilm such that periodontitis and/or any related diseases are prevented. This selective method is especially useful for inhibiting *F. nucleatum* and *P. gingivalis*, anaerobic Garm-negative lawn or any other periodontopathogens from growing into dental biofilms, presumably mediated by ROS production. Other objects are related a selective method for treating periodontal pathologies, peri-implantitis, mechano-blistering diseases, abscess, aphta, root canals etc.

It is also in the scope of the preset invention wherein the aforesaid selective method of regulating microbial cultures additionally comprises the step of introducing a chemical cofactor prior, concurrent or after the blue light emission. The chemical cofactor is selected in a non-limiting manner from an oxygen donor; medicament; cationic agents or any combination thereof. The oxygen donor is selected inter alia from oxygen, hydrogen peroxide; deuterium oxide; ozone; hydroxyl radical; singlet oxygen; superoxide anion or any combination thereof. The hereto-defined medicament is selected from antibiotic compositions, antimicrobial agents, vasoconstrictors or any combination thereof.

It is acknowledged that the method as described above, define a phototoxic procedure, wherein by emitting a blue light beam on predetermined anaerobic microorganisms a selective photochemical effect is obtained so that eradication of said cultures is solely obtained due to the susceptibility of the anaerobic bacteria to oxygen and derivatives; and further wherein by emitting a blue light beam while introducing an oxygen donor to the targeted tissue so that all flora is significantly affected. Furthermore, by emitting a blue light beam on predetermined anaerobic microorganisms a selective photochemical effect is obtained so that eradication of said cultures is solely obtained due to the susceptibility of the anaerobic bacteria to oxygen and derivatives.

The selective method may additionally comprising the step or steps of cooling the treated tissue such that its temperature of said tissue along the light emission or immediately after it shall not exceed about 42° C., e.g., between 40° C. to 45° C.

It is also in the scope of the preset invention wherein the aforesaid selective method additionally comprising applying ultrasonic vibration prior, concurrent or after the light emission.

Another object of the present invention is to present a cost effective device for selectively exerting selective photochemical effect by emitting a beam of a blue light towards a tissue to be treated; comprising means for emitting at least one blue beam as defined in any of the above, such that the temperature of said tissue is not exceeding about 42° C. along the procedure or immediately after it.

It is hence in the scope of the preset invention wherein the aforesaid device is comprised of a handpiece having a proximal portion located outside said cavity and a distal portion insertable inside said cavity; said proximal portion is manipulated by the user; said distal portion comprising a tip or a fiber optic, in communication with a blue light source; said distal portion is adapted to emit a blue light beam having a wavelength of from 400 to 550 nanometers so that a selective photochemical effect is exerted. The blue light according to the present invention is emitted by any suitable means, such as halogen lamp and xenon lamp (plasma-arc curing) with a filter, or LED.

Reference is made now to FIG. 1A, schematically presenting a lateral cross section of a blue light-emitting device (10) according to one embodiment of the present invention, characterized by an elongated tube-like envelope, comprising inter alia a blue light source of a lamp with a filter (1) or a suitable monochromator or a LED, said light is adapted to be emitted via optical track such as hollow fiber, lens system, or optic fiber (2) towards the tissue to be treated by a distal extension, as such as by a flexile fiber optic or a tip, said distal extension directed the light beam toward its end or scatter the light in multiple directions (5); an energy source, such as AD/DC adapter to a battery or adapted connection to other electric source or device (e.g., handpiece etc) (3), and an electric system (4), potentially comprising on/off shutter etc. Optical track (2) and its distal extensions (5) are selected from either flexible or rigid member, hollow fiber or any combination thereof so that a selective photochemical effect is exerted. At least a portion of the tip may be a disposable fiber optic or plastic-made ingredient. Said device and devices described below may comprise either a multiple light source and/or light trucks, or a single source or truck.

Reference is made now to FIG. 1B, schematically presenting a lateral cross section of a blue light-emitting ultrasonic scaler device (11) according to another embodiment of the present invention, adapted to emit a blue light beam towards the oral cavity so that a selective photochemical effect is exerted nearby the scaler tip.

Reference is made now to FIG. 1C, schematically presenting a lateral cross section of a blue light-emitting dental implant (12) according to yet another embodiment of the present invention, adapted to emit a blue light beam adjacent to the periodontal plaque so that a selective photochemical effect is exerted. Blue light emitting implant (12) is preferably comprised of at least one means for blue light emitting (1), e.g., either a separate emitter (here two emitters, 1 and 4), a continuous crown-like or ring-like emitter or any combination thereof. Alternatively, an orthodontic dental device, obturator or other any dental appliance is provided by still another embodiment of the present invention, and is especially adapted to emit such a blue light beam.

Reference is made now to FIG. 1D, schematically presenting a lateral cross section of a blue light-emitting tooth brush device (13) according to another embodiment of the present invention, adapted to emit a blue light beam towards the oral cavity while brushing the teeth so that a selective photochemical effect is exerted nearby the brush member.

Reference is made now to FIG. 1E, schematically presenting a view of a blue light-emitting tray (14) according to another embodiment of the present invention, adapted to emit a blue light beam towards the oral cavity so that a selective photochemical effect is exerted. Said cup may be a continuous (e.g., hat-like member) or a construction only (e.g., ring-like member) as shown.

Reference is made now to FIG. 1F, schematically presenting a lateral cross section of a blue light-emitting tray for teeth whitening (14) according to another embodiment of the present invention, adapted to emit a blue light beam towards the oral cavity so that a selective photochemical effect is exerted. Said tray (15) may emit a singular beam or a plurality of beams directed laterally, downwardly, upwardly or any combination thereof.

The aforesaid device may alternatively adapted as a tooth crown and thus be either immobilized, entrapped or anchored to a tooth or a plurality of teeth, jawbone, dental structure or between two adjacent teeth while emitting a blue light so that a selective photochemical effect is exerted.

The blue light is emitted by the aforesaid methods and devices in various manners, such as in a linear fluency, i.e., a fluency which is not significantly altered at the time or the emission; at a varied fluency, i.e., a fluency which is altered by time, e.g., by a gradual (either linear, logarithmic or other) increase, decrease etc or any combination thereof. The blue light beams are possibly emitted continuously or in a series of a plurality of ultra short or other pulses.

Said blue light-emitting devises may be additionally or alternatively combined to a chemical cofactor supplier such as oxygen delivering tube. Hence, the aforesaid devices (tray for teeth whitening or tooth brush, scaler etc) may be utilized for incorporating means for teeth whitening while emitting a blue light beam. Moreover, a photochemical effect on all flora may be obtained by coupling the administration of blue light with a sufficient supplement of oxygen donors, such as ozone, $H_2O_2$ etc. Other cofactors may also be applied in those systems.

The light emission may be initiated for a predetermined of time, as defined in the treatment procedure. Said time may be short or long, and the emission may be continuous or in pulses. The emitted light may be focused or defocused, and may be applied from the end of the distal tip of the device, and/or from its distal rim. Said distal portion may be disposable and/or for a multiple uses, and may be replaceable in the manner it is compatible with various mountable tips, such as toothbrush tip, scaler tip, flexible and thin tip for root channel treatment etc.

Reference is made thus to FIG. 1E presenting a tooth brush (16) comprising both means for emitting a blue light beam and means for releasing oxygen donors to the oral cavity such that non-selective photochemical effect is exerted, and/or teeth whitening is provided.

It is thus in the scope of the present invention to provide a useful method of whitening teeth by emitting a blue light beam and supplying an oxygen donor and/or any other cofactor to said tissue. Moreover, it is yet also in the scope of the present invention to provide a method of applying a non-selective photochemical effect on microorganism, such as non-selectively killing microorganisms in the oral cavity while whiting teeth, brushing teeth, applying the teeth with an ultrasonic treatment etc.

Reference is made now to FIG. 2A schematically presenting a fluency vs time diagram, wherein blue light is emitted as a peak, i.e., in a non-linear manner, said peak may be narrow or wide, and may be ended or endlessly continuing (See FIG. 2B). A series of two or more homogeneous or heterogeneous peaks are available, e.g., such as a series of pulses are provided (See FIG. 2C). A combination of various light wavelengths is hereto provided (See FIGS. 2D and 2E), such as a blue light (12) is followed by a white, red or other light beam (13); or such as two different beams (12 and 13) and emitted concurrently. Any combination of the above mentioned is also possible.

Moreover, it is according to another embodiment of the present invention wherein the selective method is provided by applying both steps of (a) emitting a plurality of light beams having a wavelength from 400 to 550 nanometers towards the tissue to be treated; and (b) emitting a plurality of light beams having a wavelength from 280 to 850 nanometers (white light or a monochromatic light beam, hereinafter 'white beam') towards said tissue such that a photochemical effect is exerted. The blue and/or other white beams are possible emitted in a varied fluency as defined above or in a linear/constant manner. The two light beams are possibly emitted concurrently, continuously, in a series, in pulses, or any combination thereof.

The present invention is thus prove a useful method and means to emit of blue light without exogenous photosensitizers such as to selectively treat or prevent local infections such as the periodontal diseases. Reference is made now to a set of examples for the said, which is given in an exemplary manner only.

Two anaerobic Gram-negative periopathogens: *P. gingivalis* associated with periodontal bone loss, and *F. nucleatum* associated with soft tissue inflammation, and two aerobic Gram-positive pathogens: *Streptococcus mutans* associated with dental caries and *Streptococcus faecalis* associated with root canal infections were selected as an example proving the usefulness of the present invention. Viability was tested following exposure to halogen lamp, LED or plasma-arc. The near-infrared diode laser (wavelength, 830 nm), using identical irradiation parameters was applied because clinical reports showing a beneficial effect of diode laser on periodontal pockets hypothesized that this effect is attributable to its bactericidal effect.

Bacteria: *P. gingivalis, F. nucleatum, S. mutans, S. faecalis, P. gingivalis* and *F. nucleatum* were grown and incubated at 37° C. in an anaerobic jar at <1% $O_2$ and 9-13% $CO_2$. *S. mutans* and *S. faecalis* were grown and incubated under aerobic conditions at 37° C. All the strains were sub-cultured twice before exposure to light. The bacterial concentration following 24 h incubation was standardized by dilution with sterile broth to about $5 \times 10^6$ cfu.

Bacterial samples were prepared prior to exposure to light in three experimental set-ups, as follow: (A) Bacteria in suspension: 50 µl of suspension was placed in wells of 96-well microplate, (B) Single bacteria on agar: diluted duplicates of 10 µl drops were applied to the agar surface. The appropriate dilution at which single and separate cfu grew on the agar surface was used in this set-up, and (C) Bacterial lawn: 0.1 ml of the bacterial suspension was spread evenly on agar plate.

Light sources: three commercially available visible light sources were utilize, namely halogen lamps combined with filters (400-500 nm), a xenon light source, the so-called plasma-arc (450-490 nm) and a LED (450-480 nm). In comparison, irradiation was performed at a wavelength of 830 nm, using a diode laser. The laser beam was coupled with an optical fiber and was defocused by an expanding lens at its distal end. The distance between the light source tip to the exposed sample surface was adjusted to obtain controlled power densities. The average light power was measured with a power meter over a spot of 0.7 cm diameter.

Light exposure: Samples of bacteria in suspension and single bacteria on agar were exposed in a hood under aerobic conditions to the maximum output of each light source; power densities of 260 and 416 mW/cm$^2$, using two halogen lamps (Halogen[1] and Halogen[2], respectively), to 520 mW/cm$^2$, using LED and to 1,144 mW/cm$^2$, using the plasma-arc. Every sample was exposed for 1, 1.5, 2, 2.5 or 3 minutes to each light source, bacterial strain and medium combinations, equivalent to fluences of 16 to 75 J/cm$^2$ using halogen lamps, 31 to 94 J/cm$^2$ using LED, and 69 to 206 J/cm$^2$ using the plasma-arc. Similar bacterial samples were exposed to near-infrared diode laser (wavelength, 830 nm), using light exposure parameters similar to those used for each of the three blue light sources. Spots on the bacterial lawns were exposed to light in order to determine the minimal inhibitory dose (MID), i.e., the minimum light dose required to inhibit biofilm formation. A range of power densities between 260 and 1,300 mW/cm$^2$ was obtained by placing the light sources at a distance of 1, 5 and 10 mm from the exposed surface. Exposure time ranged from 2 sec to 3 min, equivalent to fluences of 0.5 to 234 J/cm$^2$.

Determination of bacterial survival: Following exposure of the bacteria in suspension to light, samples were diluted and applied to the agar plates. Survival of these bacteria were determined, as well as of the duplicates of single bacteria on agar, by counting cfu following incubation. *P. gingivalis* and *F. nucleatum* were cultured under anaerobic conditions and *S. mutans* and *S. faecalis* under aerobic conditions at 37° C. until bacterial colonies were visible (1-5 days). The percentage of surviving bacteria was calculated in relation to the control non-exposed samples under similar experimental conditions. Biofilm inhibition in the triplicates bacterial lawn samples was defined as a halo without colony growth appearing in the light-exposed areas. All experiments in which the results of the exposed samples differed from those of the control were repeated at least twice.

Temperature changes in the medium following exposure to light: A rise in temperature during exposure to light could be a secondary factor affecting bacterial survival. For each combination of light source and medium, the temperature was measured using thermocouple electrodes, before and immediately after a three min exposure to the light.

Effect of light irradiated growth media on bacterial viability: Light irradiation could modify the growth medium. To test the indirect effect of light on bacterial viability, spots on the agar plates were exposed to maximum light source output. Agar samples were then inoculated with the bacterial strains and incubated as described above. Biofilm growth of the exposed areas was compared with that of the non-exposed surroundings.

Addition of scavengers to bacteria suspension before exposure to light: *P. gingivalis* and *F. nucleatum* were grown in media as described above. Bacterial cells were suspended in PBS prior to exposure to light as described above. The following scavengers were added to the cell suspensions: catalse, dimethylthiourea (DMTU), superoxide dismutase (SOD), ascorbic acid, desferal (iron chelating agent), PADMA (natural antioxidant), and a cocktail of all compounds, at concentration ranging from 30 to 100 µM. Then each sample was exposed in a hood under aerobic conditions to power density of 1,144 mW/cm$^2$ using halogen lamp and the plasma-arc. Every sample was exposed for 20 sec to each light source, bacterial strain and scavengers combinations, equivalent to a fluence of 23 J/cm$^2$.

Determination of bacterial survival: All four bacterial strains were tested in three experimental set-ups. Viability was assessed after bacteria in suspension or single bacteria applied to agar plates were exposed to various light sources under different conditions. In the third set-up, in which the bacteria were spread on agar plates to yield a confluent bacterial lawn, the minimal inhibitory dose was determined for each light source and strain.

Figure 3A:
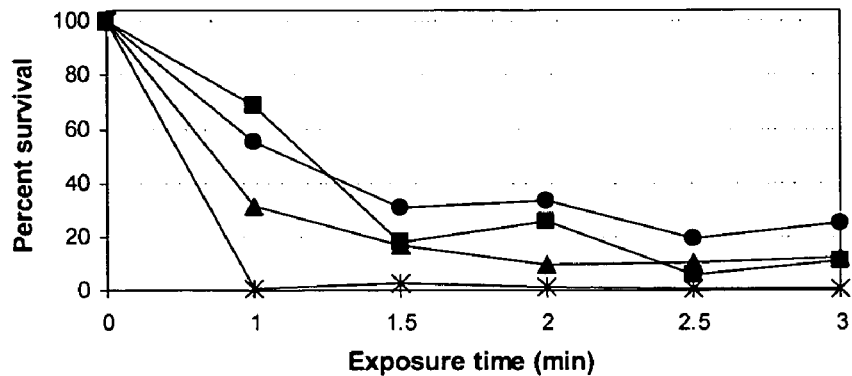
FIGS. 3A-D schematically present the effect of non-coherent blue light on viability of bacteria in suspension of *P. gingivalis* (FIG. 3A), single bacteria on agar of *P. gingivalis* (FIG. 3B), bacteria in suspension of *F. nucleatum* (FIG. 3C), single bacteria on agar of *F. nucleatum* (FIG. 3D), using halogen lamps (Halogen[1] and Halogen[2]), LED, and the plasma-arc, with exposure time of up to 3 minutes, wherein square symbols are denoted for Halogen[2]; round symbols are Halogen[1]; triangle symbols are LED and stars are denoted for plasma arc.
Figure 3B:
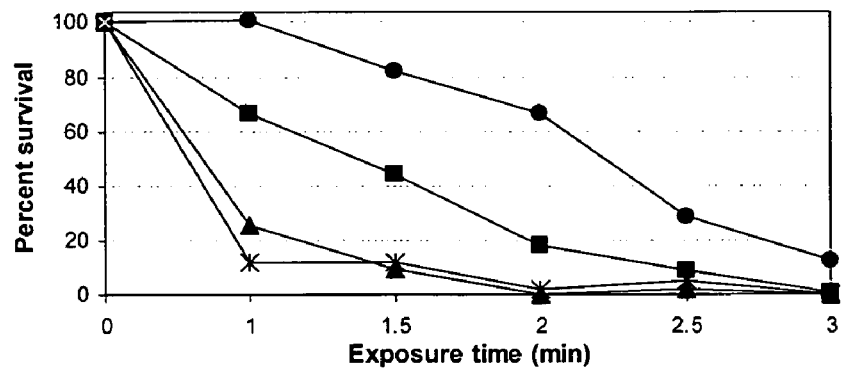
Figure 3C:
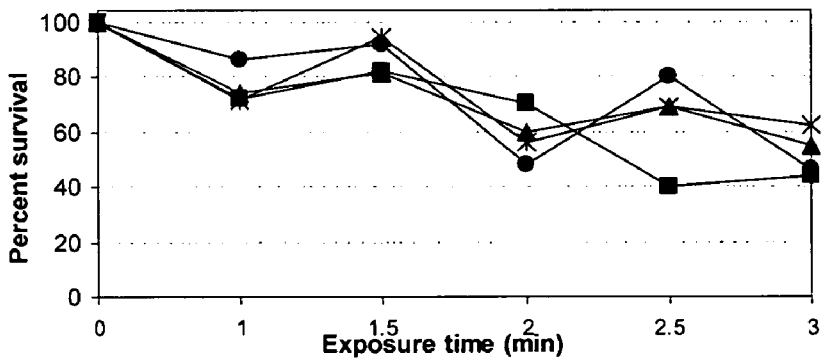
Figure 3D:
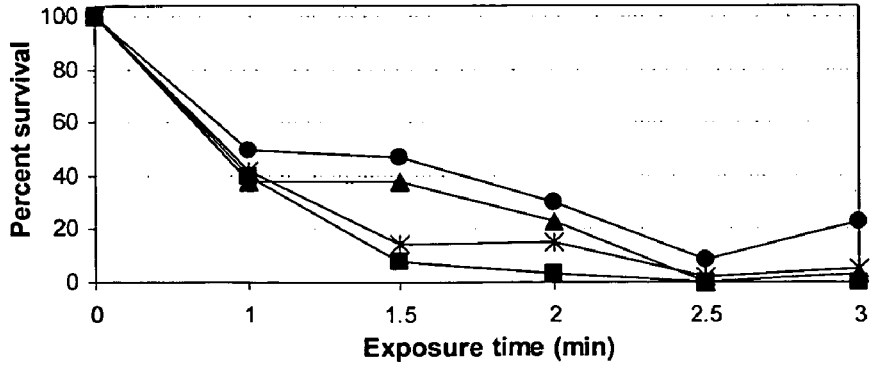

Reference is made now to FIGS. 3A to 3D, presenting bacterial viability following the exposure to blue light is expressed by percent survival of bacteria in suspension and of single bacteria on agar. Exposure to all blue light sources resulted in the reduced survival of *P. gingivalis* and *F. nuclea-* tum, which was positively correlated with exposure time. The reduced viability of *P. gingivalis* following exposure to the plasma-arc and LED was significantly higher than that after exposure to the halogen lamp (FIG. 3A, 3B). Exposure to plasma-arc light for 1 min reduced the number of *P. gingivalis* cells in suspension by 99.6% (FIG. 3A). Exposure to plasma-arc and Halogen² light of *F. nucleatum* on agar caused significantly higher cell death than exposure to the other light sources (FIG. 3D). The survival rate was lower when the *F. nucleatum* cells were exposed on agar than in suspension (FIGS. 1D, 1C). For example, single *F. nucleatum* bacteria on agar exposure to Halogen² for 2.5 minutes resulted in nearly zero survival, compared to 40% survival when *F. nucleatum* cells were in suspension.

In general, the survival rate of the Gram-positive *S. mutans* and *S. faecalis* exposed to various light sources was not affected by length of exposure in the two experimental set-ups (*S. faecalis*, p=0.205 for both factors; *S. mutans*, for length of exposure. One exception was the stimulatory effect of LED exposure on *S. faecalis* growth (not shown).

The third experimental set-up tested the effect of light on bacterial lawn. The minimum fluence required to inhibit bacterial lawn from growing into biofilm i.e., the minimal inhibitory dose (MID), is shown in Table 1. Biofilm inhibition was defined as the absence of bacterial colony formation in circular areas coinciding with those exposed to light. The exposure dose was calculated in terms of fluence, a cumulative energy density over time, by multiplying the power density by exposure time. The minimal inhibitory dose required for *P. gingivalis* and *F. nucleatum* was in the range of 16 to 62 J/cm² for all the light sources, with no significant difference between the three. The shortest exposure time (10 sec) was to the plasma arc, at a distance of 1 mm. However, the minimal inhibitory dose required for *S. mutans* and *S. faecalis* was significantly higher, 159 to 212 J/cm², and was obtained only by exposure of 90 to 150 sec to plasma-arc light. The minimal inhibitory dose required for *P. gingivalis* and *F. nucleatum* was significantly higher when the light source was placed at a distance of 10 mm from the agar surface than when at a 1 mm distance.

TABLE 1

Effect of non-coherent blue light on bacterial lawn.

| Bacterial Strain | Light Source | MID J/cm²[A] 10 mm [B] | 5 mm | 1 mm |
|---|---|---|---|---|
| *F. nucleatum* | Halogen lamp | 39 | 25 | 16[C] |
|  | LED | 41 | 47 | 22[C] |
|  | Plasma-Arc | 62 | 23[C] | 18[C] |
| *P. gingivalis* | Halogen lamp | 47 | 37 | 26 |
|  | LED | 41 | 47 | 22[C] |
|  | Plasma-Arc | 62 | 23[C] | 18[C] |
| *S. mutans* | Plasma-Arc | —[D] | 172 | 159 |
| *S. faecalis* | Plasma-Arc | —[D] | 172 | 212 |

[A]Minimal inhibitory dose (MID), i.e., the minimum fluence required to inhibit the bacterial lawn from growing into biofilm, following exposure to three light sources.
[B]The light source was located at a distance of 1, 5 or 10 mm from the agar surface.
[C]Exposure time ≦30 sec.
[D]No inhibitory effect observed.

*S. mutans* and *S. faecalis* were not affected by halogen lamp or LED light source.

The near infrared diode laser (wavelength, 830 nm) used in the three experimental set-ups, under similar exposure conditions, had no significant effect on the viability of the four bacterial species.

Figure 4:
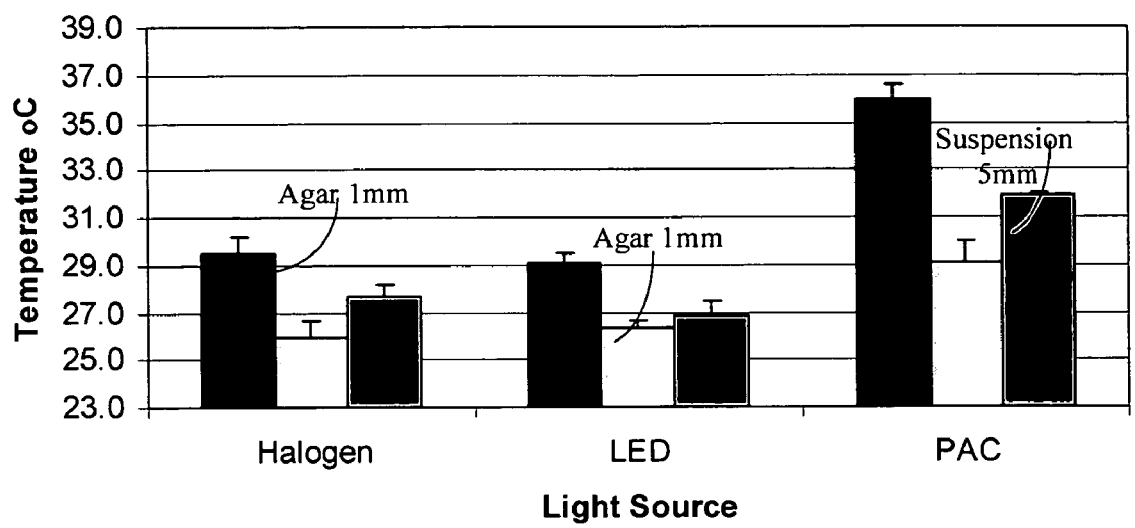
FIG. 4 schematically presents the temperature changes in bacterial medium resulting from exposure to light; thermocouple electrodes were used to measure the temperature in the BHI agar and BHI broth after maximum (3 min) exposure; the light source was located at a distance of 1 and 5 mm from the agar, and 5 mm from the liquid medium; and, FIGS. 5A-D, presenting bacterial viability following the exposure of 20 seconds to blue light wherein FIG. 5A describes the effect of plasma arc on *P. gingivalis*.
Figure 5A:
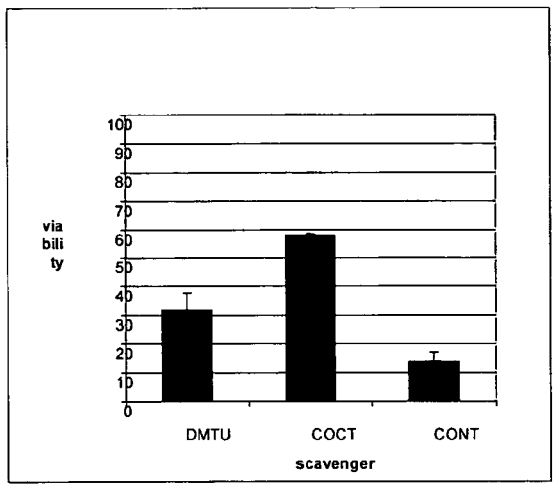
FIG. 5B presents the effect of plasma arc on *F. nucleatum*.
FIG. 5C describes the effect of halogen on *P. gingivalis*.
FIG. 5D presents the effect of halogen on *F. nucleatum*.
Figure 5B:
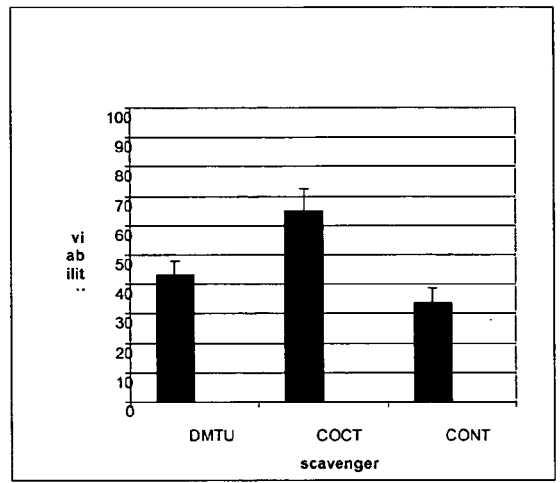
Figure 5C:
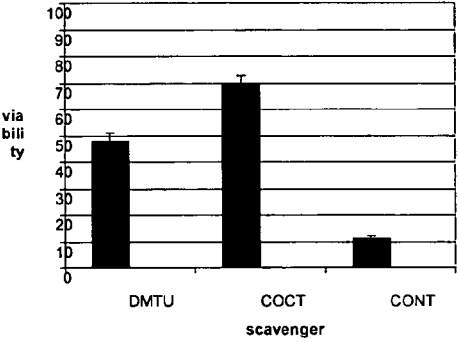
Figure 5D:
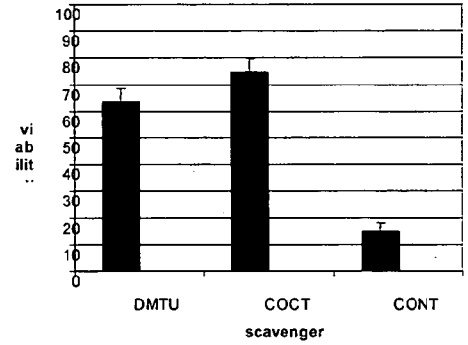

Reference is made now to FIG. 4, presenting indirect effects of light on bacterial survival via temperature and medium changes. The medium temperature immediately following 3 min of exposure to the different light sources. Each light source was placed at a distance of 5 mm from the suspension and 1 or 5 mm from the agar surface. The maximum temperature recorded was 36.6° C., with a respective change in temperature of 13° C. following exposure of the agar surface to plasma-arc light at a distance of 1 mm. The results showed a significant effect of light source and medium, with a significant interaction between the two factors. In all the combinations of light source and power density, the increase in temperature was higher in the suspensions than on the agar surface. By standardizing the changes in temperature according to power density, the differences between the effect of the light sources were only border-line significant. Moreover, a maximum increase in temperature of only 1 to 3° C. was measured using the minimal inhibitory dose values obtained by all combinations of light source and distance from the exposed surface. Also, no indirect effect of light on bacterial viability by modification of the agar medium following its exposure to light was observed.

Reference is made now to FIGS. 5A to 5D, presenting bacterial viability following the exposure to blue light in the presence of DMTU, a cocktail of scavengers, and in control, i.e., exposure to light without scavengers, is expressed as percent survival of bacteria. The scavengers cocktail (COCT) was effective in reducing phototoxicity of the plasma arc, resulted in increased survival of *P. gingivalis* (FIG. 5A) and *F. nucleatum* (FIG. 5B) to 58 and 65%. DMTU, hydroxyl radical scavenger, showed a protective effect against halogen lamp exposure, resulted in increased survival of *P. gingivalis* (FIG. 5C) and *F. nucleatum* (FIG. 5D) to 48 and 63%. There was no significant difference between the bacterial survival in the presence of DMTU and the cocktail of scavengers exposed to halogen light.

Non-coherent blue light sources such as the halogen lamp, LED, and the plasma-arc, are commonly used in dentistry for photo-polymerization of tooth colored restorative materials. Applying the same light sources, the present invention demonstrates a photochemical effect, mainly on the anaerobic Gram-negative bacteria *P. gingivalis* and *F. nucleatum* associated with periodontal diseases.

The minimal inhibitory dose for the aerobic Gram-positive *S. mutans* and *S. faecalis* proved to be 7 to 10 times higher than that for the anaerobic Gram-negative bacteria.

The minimal inhibitory dose for the Gram-positive *S. mutans* and *S. faecalis* proved to be 7 to 10 times higher than that for the Gram-negative bacteria. The lethal exposure dose was dependent not only on bacterial species but also on the experimental conditions. Higher exposure doses were required to kill bacteria in suspension. This is probably attributable to the scattering and absorption of the blue light in the suspension, reducing penetration depth. When growing on the agar surface, bacteria were killed by lower doses of light than when in suspension.

Interestingly, the bacterial lawns required even smaller doses than those necessary to kill single bacteria on agar, indicating a quorum interaction among bacterial cells. It was proposed that Gram-negative cell wall further serves as a source for secondary reaction products that accentuate the rate of cell killing. Thus, it is conceivable that the difference in the sensitivity of the bacterial cells to killing the two experimental set-ups is due to variances in the level of these secondary reaction products.

Using argon laser (wavelength, 488 to 514 nm), an oxygen-dependant mechanism killing black-pigmented bactericides was reported. The present invention teaches similar effect using a non-coherent light source; this held true not only for black-pigmented bactericides such as *P. gingivalis*, but also for *F. nucleatum*. The present invention demonstrates that the photochemical effect of visible light on bacteria is due to oxygen-dependent stimulation of reactive oxygen species production.

The involvement of a cell associated photochemical mechanism is also supported by the present invention, showing neither an indirect effect of light on the medium nor an increase in temperature that could damage bacteria, for example by causing thermal coagulation of the bacteria, following exposure to blue light. The present invention discloses that low power red light or near-infrared light exerted no significant antibacterial affect, wherein under certain conditions, an increase in bacterial growth was detected. This is in agreement with other results provided by the applicants, using near-infrared laser, where no effect on any of the bacteria tested was observed.

The present invention further teaches that commercially available blue light sources initially adapted to photo-polymerize dental composite materials, could also serve for the selective reduction of periopathogenic bacteria. The photochemical effect may be greater under clinical conditions where bacteria are under stress than under ideal in vitro conditions.

It is acknowledged in this respect that oral biofilm are affected by the blue light source owing to differential killing of these periopathogenic bacteria.

What is claimed is:

1. A selective photochemical method of treating microbial diseases in local infections by selectively damaging specific bacteria, said method comprising step of emitting for a time period of up to 3 minutes a beam of a blue light towards the tissue to be treated; said beam of a blue light characterized by (i) wavelength from 400 to 550 nanometers; (ii) energy density in the range of 0.5 to 234 J/cm$^2$; thereby forming reactive oxygen species (ROS) and selectively damaging said specific bacteria;
    said energy density is provided such that an irreversible thermal damage to said tissue during and after said step of emitting blue light is prevented;
    wherein said step of emitting said blue light beam is performed without (i) any exogenous photosensitizers; and, (ii) any thermal coagulation of said bacteria.

2. The selective method according to claim 1, wherein the local infections are selected from the body cavities, interfaces, ear, nose, throat, vagina or orifices; and further wherein the microbial diseases are selected from bacterial, viral or fungal diseases.

3. The selective method according to claim 1, useful for inhibiting predetermined bacteria from growing into biofilm such that periodontitis is prevented.

4. The selective method according to claim 1, useful for inhibiting predetermined anaerobic microorganisms from growing into biofilm such that periodontitis is prevented.

5. The selective according to claim 1, wherein said bacteria is anaerobic bacteria selected from a group consisting of *F. nucleatum, P. gingivalis* or any other anaerobic bacteria.

6. The selective method according to claim 1, wherein said method is useful for treating periodontal pathologies, peri-implantitis, mechano-blistering diseases or abscess.

7. The selective method according to claim 1, useful for exerting photochemical effect in root canals.

8. The selective method according to claim 1, wherein said step of emitting said blue light is performed in different fluences.

9. The selective method according to claim 1, wherein said blue light beam is emitted in a series of pulses.

10. The selective method according to claim 1, additionally comprising steps of:
    emitting a plurality of light beams having a wavelength from 400 to 550 nanometers towards the tissue to be treated; and,
    emitting a plurality of light beams having a wavelength from 280 to 850 nanometers towards said tissue such that a photochemical effect is exerted.

11. The selective method according to claim 10, wherein either the blue or other light beams are emitted in different fluences.

12. The selective method according to claim 10, wherein the two light beams are emitted concurrently, in a series, continuously, in pulses, or any combination thereof 13. The selective method according to claim 1, wherein said method additionally comprising the step of introducing a chemical cofactor prior, concurrent or after the blue light emission.

14. The selective method according to claim 13, wherein said chemical cofactor is selected from a group consisting of oxygen donor; medicament; cationic agent or any combination thereof.

15. The selective method according to claim 14, wherein said oxygen donor is selected from a group consisting of hydrogen peroxide; singlet oxygen; deuterium oxide; hydroxyl radical; superoxide anion or any combination thereof.

16. The selective method according to claim 14, wherein said oxygen donor is ozone.

17. The selective method according to claim 14, wherein said medicament is selected from a group a group consisting of antibiotic compositions, antimicrobial agents, vasoconstrictors; or any combination thereof.

18. The selective method according to claim 1, additionally comprising applying ultrasonic vibration prior, concurrent or after said step of emitting light.

19. The selective method according to claim 1, wherein said bacteria is anaerobic bacteria; further wherein said selectively, damaging said specific kind of bacteria, is regulated by varying said energy densities delivered to said tissue.

20. The selective method according to claim 1, wherein said bacteria is anaerobic bacteria; further wherein said selectively, damaging said specific kind of bacteria, is regulated by varying the concentration of ROS.

21. A photochemical method for reducing the flora of microbial pathogens in local infections, said method comprising steps of:
    emitting for a time period of up to 3 minutes a beam of a blue light towards the tissue to be treated; said beam characterized by (i) wavelength from 400 to 550 nanometers; (ii) fluence in the range of 0.5 to 234 J/cm$^2$; thereby forming reactive oxygen species (ROS) and damaging said flora;
        said energy density is provided such that an irreversible thermal damage to said tissue during and after said step of emitting blue light is prevented; and,
    b. introducing an oxygen donor to said tissue such that all said flora is significantly damaged;
    wherein said step (a) of emitting said blue light beam is utilized without any exogenous photosensitizers such that (i) a photochemical effect is exerted; and, (ii) no thermal coagulation of said flora is obtained.

22. The method according to claim 21, additionally comprising step of regulating the damage to said flora by varying said energy densities delivered to said tissue.

23. The method according to claim 21, additionally comprising step of regulating the damage to said flora by varying the concentration of ROS.

* * * * *